United States Patent [19]

Domb

[11] Patent Number: 5,340,588

[45] Date of Patent: * Aug. 23, 1994

[54] LIPOSPHERE CARRIERS OF VACCINES

[75] Inventor: Abraham J. Domb, Baltimore, Md.

[73] Assignee: Nova Pharmaceutical Corporation, Baltimore, Md.

[*] Notice: The portion of the term of this patent subsequent to Feb. 23, 2010 has been disclaimed.

[21] Appl. No.: 825,287

[22] Filed: Jan. 23, 1992

Related U.S. Application Data

[63] Continuation of Ser. No. 607,544, Nov. 8, 1990, abandoned, which is a continuation-in-part of Ser. No. 435,546, Nov. 13, 1989, abandoned.

[51] Int. Cl.$^5$ .................. A61K 37/22; A61K 39/02
[52] U.S. Cl. .................. 424/450; 424/193.1; 424/812
[58] Field of Search .................. 424/450, 87

[56] References Cited

U.S. PATENT DOCUMENTS

| | | | |
|---|---|---|---|
| 3,004,892 | 10/1981 | Hainsworth et al. | 424/502 |
| 3,159,545 | 12/1964 | Kidwell et al. | 424/1.1 |
| 3,159,600 | 12/1964 | Watkins | 528/27 |
| 3,804,776 | 4/1974 | Yazawa et al. | 427/213.3 |
| 3,957,971 | 5/1976 | Oleniacz | 424/70 |
| 3,993,754 | 11/1976 | Rahman et al. | 514/12 |
| 4,010,038 | 3/1977 | Iwasaki et al. | 66/22 |
| 4,025,455 | 5/1977 | Shackle | 428/402.21 |
| 4,029,762 | 6/1977 | Galanos et al. | 424/87 |
| 4,089,801 | 5/1978 | Schneider | 264/4.1 |
| 4,145,410 | 3/1979 | Sears | 424/450 |
| 4,168,308 | 9/1979 | Wretlind et al. | 379/319 |
| 4,186,183 | 1/1980 | Steck et al. | 424/450 |
| 4,201,767 | 5/1980 | Fullerton et al. | 424/450 X |
| 4,224,179 | 9/1980 | Schneider | 264/4.2 |
| 4,235,871 | 11/1980 | Papahadiopoulos et al. | 424/450 |
| 4,280,996 | 7/1981 | Okamoto et al. | 514/78 |
| 4,298,594 | 11/1981 | Sears et al. | 424/450 |
| 4,310,506 | 1/1982 | Baldeschwieler et al. | 424/1.1 |
| 4,317,743 | 3/1982 | Chang | 428/402.21 |
| 4,331,654 | 5/1982 | Morris | 424/450 |
| 4,332,796 | 6/1982 | Los | 514/157 |
| 4,349,529 | 9/1982 | Morcos et al. | 424/1.1 |
| 4,356,167 | 10/1982 | Kelly | 209/37 |
| 4,377,567 | 3/1983 | Geho | 424/1.1 |

(List continued on next page.)

FOREIGN PATENT DOCUMENTS

| | | |
|---|---|---|
| 0042249 | 10/1981 | European Pat. Off. |
| 0177368 | 4/1986 | European Pat. Off. |
| 0209870 | 1/1987 | European Pat. Off. |
| 0274431 | 7/1988 | European Pat. Off. |

(List continued on next page.)

OTHER PUBLICATIONS

Friedman, et al., *Drug Development and Industrial Pharmacy* 13(9–11), 2067–2085 (1987).

Gasco, et al., *Il Farmaco-Ed. Pr.* 43(10) 326 (1987).

Gasco, et al., *International Journal of Cosmetic Science* 10(6), 263–269 (1988).

Kawamata, et al., *J. Pharm. Sci.* 76(11), S275, Abstract No. 04–W–19 (1987).

Schmidt, et al., *Acta Pharmaceutical Technologica* 38(1), 34 (1989).

(List continued on next page.)

*Primary Examiner*—Thurman K. Page
*Assistant Examiner*—Neil Levy
*Attorney, Agent, or Firm*—Kilpatrick & Cody

[57] ABSTRACT

Solid, water-insoluble liposheres including a solid hydrophobic core, having a layer of a phospholipid embedded on the surface of the core, that contain an antigen are disclosed for use in immunizing an animal. The antigen (or "immunogen"), alone or in combination with a carrier, can form the core, be attached to or within the phospholipid, or both. Liposheres containing antigens are prepared by two general procedures, either melt preparation or solvent preparation. The resulting liposheres have several advantages over other delivery systems, including emulsions, vesicles and liposomes, including stability, low cost of reagents, ease of manufacture, high dispersibility in an aqueous medium, a release rate for the entrapped substance that is controlled by the phospholipid coating and the carrier.

31 Claims, 5 Drawing Sheets

U.S. PATENT DOCUMENTS

| | | | |
|---|---|---|---|
| 4,404,183 | 9/1983 | Kawata et al. | 514/420 |
| 4,434,153 | 2/1984 | Urquhart et al. | 424/469 |
| 4,438,052 | 3/1984 | Weder et al. | 264/4.6 |
| 4,439,194 | 3/1984 | Harwood et al. | 424/436 |
| 4,446,165 | 5/1984 | Roberts | 426/602 |
| 4,448,765 | 5/1984 | Ash et al. | 285/119 |
| 4,460,560 | 7/1984 | Tokes et al. | 424/1.1 |
| 4,485,054 | 11/1984 | Mezei et al. | 264/4.6 |
| 4,492,720 | 11/1985 | Mosier | 427/213.3 |
| 4,515,736 | 5/1985 | Deamer | 264/4.3 |
| 4,544,545 | 10/1985 | Ryan et al. | 424/1.1 |
| 4,563,354 | 1/1986 | Chang et al. | 424/195.1 |
| 4,610,868 | 9/1986 | Fountain | 424/1.1 |
| 4,622,219 | 7/1986 | Haynes | 424/450 |
| 4,725,442 | 2/1988 | Haynes | 424/490 |
| 4,752,485 | 6/1988 | Sharma et al. | 426/99 |
| 4,761,288 | 8/1988 | Mezel | 424/450 |
| 4,794,000 | 12/1988 | Ecanow | 424/457 |
| 4,797,288 | 1/1989 | Sharma et al. | 424/476 |
| 4,804,548 | 2/1989 | Sharma et al. | 426/92 |
| 4,816,247 | 3/1989 | Desai et al. | 514/216 |
| 4,828,857 | 5/1989 | Sharma et al. | 426/285 |
| 4,880,634 | 11/1989 | Speiser | 424/450 |
| 4,894,233 | 1/1990 | Sharma et al. | 424/440 |
| 4,894,234 | 1/1990 | Sharma et al. | 424/440 |
| 4,911,928 | 3/1990 | Wallach | 424/450 |
| 4,914,084 | 4/1990 | Ecanow | 514/6 |
| 4,929,508 | 5/1990 | Sharma et al. | 424/439 |
| 4,933,183 | 6/1990 | Sharma et al. | 424/439 |
| 4,935,242 | 6/1990 | Sharma et al. | 429/19 |
| 4,963,363 | 10/1990 | Forssen | 424/450 |
| 4,963,367 | 10/1990 | Ecanow | 424/485 |
| 4,973,465 | 11/1990 | Baurain et al. | 424/406 |

FOREIGN PATENT DOCUMENTS

| | | |
|---|---|---|
| 2601207A1 | 7/1976 | Fed. Rep. of Germany . |
| WO83/00294 | 2/1983 | PCT Int'l Appl. . |
| WOA8500011 | 1/1985 | PCT Int'l Appl. . |
| 2135647A | 9/1984 | United Kingdom . |

OTHER PUBLICATIONS

Wang, et al., *J. Pharm. Sci.* 76(11), S305, Abstract No. 07-W-21 (1987).

Wang, et al., *J. Pharm. Sci.* 76(11), S305, Abstract No. N 07-W-22.

Sasaki, et al., *J. Pharm. Dyn.* 7, 120–130 (1984).

Venkatesh, et al., *J. Pharm. Sci.* 76(11), S305, Abstract No. N 07-W-19.

Gao and Huang, *Biochim. Biophys. Acta* 897, 377–383 (1987).

LIPOSPHERE CARRIERS OF VACCINES

This is a continuation of application Ser. No. 07/607,544 filed on Nov. 8, 1990, now abandoned, which is a continuation-in-part of U.S Ser. No. 07/435,546, entitled "Liposheres for Controlled Delivery of Substances," filed on Nov. 13, 1989, by Abraham J. Domb now abandoned.

BACKGROUND OF THE INVENTION

An immune response can be induced against an almost limitless variety of substances. There are two principal types of immune responses: cell mediated responses and humoral responses. In both situations, an antigen, or foreign substance, is recognized by specific receptors on the surfaces of lymphocytes. Humoral responses are characterized by the production of antibodies specifically directed against regions of the antigen known as epitopes. Under normal circumstances, antigen recognition results in the destruction and/or removal of the antigen from the animal.

Induction of antibody (Ab) formation and of specific cellular responses is referred to as immunization even when infectious agents are not involved. Vaccination usually refers to immunization in which a suspension of infectious agents (or parts thereof) is administered to an animal to induce resistance to the disease caused by the infectious agents.

The intentional vaccination of individuals to protect against disease began in the eighteenth century with the inoculation of scrapings from persons infected with cowpox to protect against the related disease smallpox. Techniques have improved substantially since that time, leading to a decreased incidence of side effects due to reactions against contaminants in the vaccine and to the elicitation of an immunogenic response against materials not normally eliciting an immune response. These enhanced effects have been achieved by altering the antigen by attaching it to a carrier molecule, by chemical modification, and by administering it in conjunction with a vehicle increasing the immunological response to the antigen (referred to as an adjuvant).

The most well known example of these vehicles enhancing an antigenic response is Freund's adjuvent, a water-in-oil emulsion containing tubercle bacillus, or the purified lipid component of the bacillus. The amount of antigen incorporated determines whether antibodies or a cell mediated response is elicited. A related example is aluminum hydroxide and nonpyogenic liposomal lipid A, described, for example, by Richards, et al., *Vaccine* 7, 505–512 (Dec. 1989).

Liposomes have also been used for encapsulation and administration of antigens, for example, as described by Richards, et al., "Development of liposomes as carriers for a human malaria peptide vaccine" in *Liposomes as Drug Carriers* ed. B. Gregoriadis pp. 235–241 (John Wiley & Sons Ltd. 1988). Although enhancing the immunological response, probably by targeting the antigen to the lymphocytes which phagocytize the liposomes and allowing the administration of higher doses of antigen and adjuvant, the problems with using liposomes and vesicles as delivery devices are manifold. They are difficult to prepare, unstable, and can only be used for encapsulation of certain types of materials.

Many infectious agents have proven difficult, if not impossible, to elicit an immunological response to that is effective in preventing subsequent infection by the agent. An example of such an agent is the human immunodeficiency virus. Other agents, such as toxins and agents used in biological and chemical warfare, are not immunogenic in the form to which a person or other animal would be exposed.

It is therefore an object of the present invention to provide a composition and method to administer antigens for immunization of an animal.

It is a further object of the present invention to provide a composition and method to effect or enhance immunization of an animal against an antigen that does not normally produce a good immunological response.

It is another object of the present invention to provide a composition, and method of use thereof, for immunization of an animal against an antigen that is easy to prepare and stable for an extended period of time prior to use and in vivo.

SUMMARY OF THE INVENTION

Solid, water-insoluble liposheres including a solid hydrophobic core, having a layer of a phospholipid embedded on the surface of the core, that contain an antigen are disclosed for use in immunizing an animal. The antigen (or "immunogen"), alone or in combination with a carrier, can form the core, be attached to or within the phospholipid, or both.

Liposheres containing antigens are prepared by two general procedures, either melt preparation or solvent preparation. For melt preparation, the antigen is dispersed or dissolved in a molten carrier containing phospholipid. An aqueous buffer, pre-incubated at a temperature higher than the melting temperature of the carrier, is added and the mixture shaken until a homogenous suspension is obtained, followed by rapid cooling of the preparation to below the melting temperature. For solvent preparation, the antigen is dissolved and/or core material is dissolved or dispersed in a solvent, and added to phospholipid along with an aqueous solution, followed by shaking until a homogeneous suspension is obtained.

The resulting liposheres have several advantages over other delivery systems, including emulsions, vesicles and liposomes, including stability, low cost of reagents, ease of manufacture, high dispersibility in an aqueous medium, a release rate for the entrapped substance that is controlled by the phospholipid coating and the carrier.

BRIEF DESCRIPTION OF THE DRAWING

FIG. 3 are graphs of the antibody produced (ELISA units) as a function of the time (weeks) after immunization (at zero time and again four weeks later) with liposphere formulations containing lipid A (40 μg) and R32NS1 (100 μg) for IgG antibodies (FIG. 3A) and IgM antibodies (FIG. 3B) to lipid A.

FIG. 4 are graphs of the white blood cell (WBC) count (x1000) over time (days) of rabbits injected intramuscularly with liposheres containing R32NS1 (125 μg/dose) and lipid A (60 μg/dose) (FIG. 4A) or free lipid A (60 μg) (FIG. 4B) over time (days).

FIG. 5 are graphs of the antibody produced (ELISA units) as a function of the time (weeks) after immunization (at zero time and again four weeks later) with liposphere formulations containing lipid A and a malarial antigen (R32tet SKB) in combination with alum (FIG. 5A, mean titer for group, --*--) or liposomes containing lipid A and the malarial antigen in combination with alum (FIG. 5A, mean titer for group, --*--. The individual responses are shown in FIG. 5B.

The mean antibody titer for each of the rabbits in the two groups is shown in FIG. 5A.

DETAILED DESCRIPTION OF THE INVENTION

Liposphere formulations are prepared for use in releasing antigen following administration to a human or other animal using standard procedures for enteral, parenteral, or transbuccal or transdermal administration of vaccine, which provide enhanced immune response. The liposheres are formed of a core that is solid at about room temperature surrounded by a layer of phospholipid embedded in the surface of the solid core. The antigen (or antigens) are incorporated as, or within, the solid core, in the phospholipid layer, on the surface of the phospholipid layer, or a mixture thereof. The liposheres are formulated to provide immediate release, sustained released, "pulsed", or delayed release of antigen following administration.

PREPARATION OF LIPOSHERES

The preparation and modification of liposheres is described first with reference to the following general descriptions and then with reference to the following non-limiting examples of the preparation and administration of liposheres as vaccines.

SELECTION OF THE SOLID CORE OF THE LIPOSPHERE

In the preferred embodiment, the liposphere contains a core that has a melting temperature in excess of room temperature, which is prepared by choosing an antigen to be delivered that is a solid at room temperature (for example, approximately 30° C.), or by mixing the antigen to be delivered in a carrier to produce a mixture that is a solid at room temperature, about 25° C. (for example, having a melting point of approximately 30° C.). The melting point of the antigen, alone or in combination with the carrier, should preferably be below 120° C. The antigen, or antigen and carrier, should also be stable in the liquid form when mixed with hot aqueous media.

The carrier must be compatible with the antigen. Suitable pharmaceutical solid carriers are inert hydrophobic biocompatible materials with a melting range between 30° and 120° C. Examples are natural, regenerated, or synthetic waxes such as beeswax and carnauba wax; cholesterol; fatty acid esters such as ethyl stearate, isopropyl myristate, and isopropyl palmitate; high molecular weight fatty alcohols such as cetostearyl alcohol, cetyl alcohol, stearyl alcohol, and oleyl alcohol; solid hydrogenated castor and vegetable oils; hard and soft paraffins; hard fat such as tristearin; biodegradable polymers such as polycaprolactone, polyamides, polyanhydrides, polycarbonates, polyorthoesters, polylactic acids, and copolymers of lactic acid and glycolic acid; cellulose derivatives and mixtures thereof. These materials are known to those skilled in the art and most are commercially available, as demonstrated by the extensive list of suitable carrier materials in Martindale, *The Extra Pharmacopoeia,* The Pharmaceutical Press, 28th Edition pp 1063-1072 (1982). The synthetic polymers are preferred where controlled release over a period of time or after discrete time intervals is desired.

The release rate of the antigen from the liposphere is dependent in part upon the composition of the core, as well as the outer phospholipid layer, and can be altered by varying the compositions appropriately.

The antigen can be preincorporated into microparticles of a hydrophobic solid phase, such as tristearin (melting point 65° C. to 72° C.), that can then be incorporated into lipospheres with a carrier having a lower melting point, such as ethyl stearate (melting point 35° C.), to avoid melting the tristearin particles containing the antigen. In this form, the tristearin-antigen particles are the hydrophobic antigen which is dispersed in the ethyl stearate liposphere. The formulations can then be freeze dried with standard techniques and reconstituted prior to use .

SELECTION OF THE PHOSPHOLIPID COATING

The solid core of the liposphere is coated with one or more phospholipids that are embedded into the surface of the solid core during manufacture. Mixtures of two or more phospholipids can be used to vary the surface properties and reactivity of the liposphere. The antigen can be incorporated into the phospholipid, as well as or instead of the core, or subsequently adhered to the phospholipid, by selection of phospholipid and antigen having the appropriate chemical properties.

PHOSPHOLIPID

A phospholipid is a phosphorylated diacylglyceride molecule or its derivative. The parent structure is diacylglycerol phosphate, or phosphatidic acid. Phosphatidyl choline (lecithin) is the choline ester of phosphorylated diacylglyceride. Synthetic lecithins are available with acyl chain lengths ranging from 4 to 19 carbons. The preferred lecithins for biological applications are those with alkyl chain lengths in the biological range (10 to 18 carbons). Naturally occurring lecithin can be obtained from a variety of sources such as egg, bovine heart, or soya bean. Unsaturated lecithins (dioleoyl; dilinoleoyl; alpha-palmitoyl, beta oleoyl; alpha palmitoyl, beta linoleoyl; and alpha oleoyl, beta palmitoyl), dianachidonyl lecithin (highly unsaturated and a prostaglandin precursor), and alpha palmito beta myristoyl lecithin are also available.

A molecule somewhat structurally related to phosphatidic acid, sphingomyelin, is also suitable for use in the coating of lipospheres.

Certain phospholipids, such as phosphatidic acid, phosphatidyl serine, phosphatidyl inositol, cardiolipin (diphosphatidyl glycerol), and phosphatidyl glycerol, can react with calcium in serum, causing aggregation or the binding of lipospheres to cell membranes. These reactions can be minimized by combining these phospholipids with non-calcium binding phospholipids such as phosphatidyl choline. Phosphatidic acid can be isolated from egg or prepared synthetically (dimyristoyl, dipalmitoyl and distearoyl derivatives are available from Calbiochem). Bovine phosphatidyl serine is also available commercially (Sigma Chemical Co., St. Louis, Mo.). Phosphatidyl inositol can be isolated from plant or bovine sources. Cardiolipin can be purified from bovine or bacterial sources. Phosphatidyl glycerol can also be purified from bacterial sources or prepared synthetically.

Phosphatidyl ethanolamine in the pure state self-aggregates in a calcium-independent fashion, and is believed to have strong tendencies to aggregate with cell membranes, should be used in combination with non-aggregating phospholipids. Phosphatidyl ethanolamine is commercially available, isolated from egg, bacteria, bovine, or plasmalogen or as the synthetic dioctadecanoyl, dioleoyl, dihexadecyl, dilauryl, dimyristoyl and dipalmitoyl derivatives.

STEROIDS

Steroids such as cholesterol (a natural constituent of membranes), estrogens (such as estriol, estrone, estradiol and diethylstilbestrol), and androgens (such as androstenedione and testosterone) cannot function alone as the liposphere coating but may be incorporated into the phospholipid surface coating, as well as serve as the core material.

AMPHIPHILES

Amphiphiles can be added to the phospholipid coating to alter the surface charge on the liposphere. Examples of amphiphiles that produce a positive charge on the coating are protonated long chain alkyl amines such as stearylamine or the corresponding secondary, tertiary or quaternary substituted amines. Examples of amphiphiles that produce a negative charge are arachidonic acid and other fatty acids.

SURFACTANTS

The phospholipids can be substituted in part with surfactants such as Tween TM (a hydrophilic class of surfactants), Span TM (a hydrophobic class of surfactants), and polyethylene glycol surfactants.

SELECTION OF ANTIGEN

The antigen can be any compound eliciting a desired immunogenic response when administered to an animal in combination with the lipospheres. The antigen may be bacterial, vital, fungal or parasitic in origin, produced naturally and isolated, by recombinant engineering, or chemically synthesized. The bacteria, virus or fungi can be live, attenuated, or killed, administered whole or in part. The antigen may also be a chemical or organic molecule or composition, such as pollen. The antigen may be administered alone or bound to a carrier or chemically modified (for example, chemically cross-linked to form a larger molecule or in combination with an adjuvant. An immunogenic response is characterized as the production of cells having receptors specifically binding to the antigen (T lymphocytes) or cells producing antibodies specifically recognizing the antigen (B lymphocytes).

The amount of antigen incorporated into the lipospheres and administered to an animal can be experimentally determined using standard techniques for administration and measurement of immune response, either cell mediated or antibody titer. As used herein, an antigen is an agent eliciting either, or both, a cell mediated immune response or a humoral immune response.

The lipospheres may also be administered to block an immune response. For example, antibody or antigen may be administered to remove either a circulating antigen, or antibody, from the bloodstream. This is a frequently used technique for desensitization of people with allergies or to inhibit a reaction to a chemical such as an antibiotic or toxin.

For live organisms, special precautions must be taken not to destroy the antigenicity of the organism during the preparation of the liposphere. This can be accomplished, for example, by incorporating the antigen into a carrier having a low melting point such as trimyristin, ethyl stearate, or trilaurin, or by incorporating the virus in a solvent that does not kill or denature the antigenicity of the organism.

Examples of antigens used in the following examples include antigens used in malarial vaccines, such as antigens incorporating NANP epitopes from repeat region of circumsporozoite protein of *Plasmodium falciparum* sporozoite, such as R32NS1, and antigens used in vaccines against Gram-negative bacteria, such as Lipid A from lipopolysaccharide of Gram-negative bacteria, for example, *Salmonella minnesota* R595.

SELECTION OF ADJUVANTS

The antigen can be incorporated into the solid core alone or in combination with an adjuvant. The core material, the phospholipid, or the entire liposphere may act as an adjuvant. An adjuvant is any compound enhancing the immune response to the antigen, either specifically or non-specifically. Examples of adjuvants are bacteria, either modified live or killed, or immunogenic parts thereof, such as the capsule, alone and in combination with lipid materials. An adjuvant that is routinely used is alum. Examples of adjuvants of bacterial origin are Lipid A and tuberculin bacteria.

PREPARATION OF LIPOSPHERES

Lipospheres containing antigens are prepared by either of two general procedures depending on the chemical characteristics of the antigen. For hydrophobic or hydrophilic antigens, for example, the antigen may be dispersed or dissolved in a molten carrier containing phospholipid. An aqueous buffer, pre-incubated at a temperature higher than the melting temperature of the carrier, is added and the mixture shaken until a homogenous suspension is obtained, followed by rapid cooling of the preparation to below the melting temperature. For hydrophilic antigens, the antigen can be dissolved in the aqueous buffer pre-incubated to a temperature higher than the melting temperature of the vehicle and added to the molten mixture of vehicle and phospholipid, followed by shaking until a homogeneous suspension is obtained and rapid cooling of the formulation to below the melting temperature.

Suitable methods of mixing the suspension include mechanical shaking or stirring, fine mixing using homogenizing and sonication.

Another method of preparation of lipospheres involves the use of solvent. The antigen, carrier, and phospholipid in an organic solvent are mixed, for example, in ethanol, ethyl acetate, or methylene chloride added to a round bottomed flask. The solvent is then evaporated, and the resulting solid is mixed with an appropriate amount of buffer and rotation continued until a homogeneous mixture is obtained. The temperature is then reduced to 10° C. with continuation rotation for approximately five minutes to form a milky suspension of lipospheres.

In an aqueous solution, the lipospheres form a uniform fine dispersion of microspheres coated with a layer of a phospholipid, with the hydrophobic side of the phospholipid embedded in the outermost layer of the solid hydrophobic core and the hydrophilic side at the aqueous interface. The particle size, particle distribution, and phospholipid coating can be altered by varying the concentration and properties of the solid vehicle, the lipid, and the mixing method. For intravenous injections, particles should be less than five microns. For subdermal or intramuscular injections, the particle is preferably less than 250$\mu$ in diameter. Larger particle sizes can be used for oral formulations. For controlled drug delivery, the average particle size of the liposphere should be greater than one micron.

A preferred range of antigen to carrier to phospholipid is from 1:0:0.01 to 1:100:100. Other biologically active materials can also be encapsulated in the lipospheres during either melt preparation or solvent preparation.

The lipospheres are distinct from microdroplets, vesicles or liposomes since the lipospheres have solid inner cores at the temperature at which they are used (usually body temperature). The temperature referred to as the "melting temperature" is defined as the temperature at which the solid core material becomes liquid, and the phospholipid coating is entrapped and fixed to the particle surface. The lipospheres are distinct from microspheres of uniformly dispersed material in homogenous polymer since they consist of at least two phases, the inner solid particle and the outer layer of phospholipid.

The combination of solid inner core with phospholipid exterior confers several advantages on the lipospheres as compared with conventional microspheres and microparticles, including high dispersibility in an aqueous medium, and a release rate for the entrapped substance that is controlled by the phospholipid coating and the carrier. There are also many advantages over other dispersion based delivery systems. Lipospheres have increased stability as compared to emulsion based delivery systems, including vesicles and liposomes, and are more effectively dispersed than most suspension based systems. Further, the substance to be delivered does not have to be soluble in the vehicle since it can be dispersed in the solid carrier. Lipospheres also have a lower risk of reaction of substance to be delivered with the vehicle than in emulsion systems because the vehicle is a solid inert material. Moreover, the release rate of the antigen from the lipospheres can be manipulated by altering either or both the inner solid vehicle or the outer phospholipid layer. Lipospheres are also easier to prepare than vehicles such as liposomes, and are inherently more stable. Stability has become the major problem limiting the use of liposomes, both in terms of shelf life and after administration to a patient. Liposomes and vesicles do not remain intact or available in vivo for more than a few hours to a couple of days. Lipospheres can also be prepared from inexpensive mixtures of phospholipids and do not require special, highly pure phospholipids.

METHODS OF USE OF LIPOSPHERES CONTAINING ANTIGEN

The lipospheres are administered to the patient enterally (orally, nasally, rectally), parenterally (intravenously, subcutaneously, intramuscularly, intraperitoneally), transbuccally or transdermally in the appropriate carrier for administration to the patient of an antigen. The dosage is determined by the release rate of the antigen in combination with the immunogenicity of the antigen.

The vaccine can be administered in a single dose or in repeated dosages. Alternatively, the core material can be selected to provide release over a sustained period of time, or at a discrete time(s). Mixtures of lipospheres releasing at different discrete times can be used to achieve the same effect as multiple injections. Most vaccines are administered initially two or three times over a two to three month interval to maximize antibody production. The preferred core material for delayed release is a polymer such as polylactide.

The liposphere formulations are stored in aqueous buffer or freeze dried in the freezer, refrigerator or room temperature, depending on the nature of the antigen. It is preferred to store the formulations as a freeze dried powder.

The method of preparation of lipospheres, and resulting lipospheres containing antigen, described herein is simple and is characterized by high loading, reproducibility, versatility, low cost, and stability. The method and compositions are further illustrated by the following non-limiting examples.

EXAMPLE 1: Method of Preparation of Lipospheres Containing the Immunogen Lipid A The lipid A used in this study was primarily monophosphoryl lipid A (a glycophospholipid antigen) from *Salmonella Minnesota* R595, supplied by List Biological Laboratories, Inc., Campbell, Calif.

To a 20 ml vial was added ethyl stearate (300 mg, melting point 34°–35° C.), L-$\alpha$-lecithin (150 mg), and lipid A (2 mg). The vial was heated to 40° C. to melt the ethyl stearate and disperse the lipid A. Warm phosphate buffer (0.1 M PBS pH 7.4 35°–40° C., 10 ml) was added and the formulation was mixed well by vigorous hand shaking and by vortexing for about 5 min. The uniform milky-appearing formulation was immediately cooled to a temperature below 20° C. by immersing the vial in a dry ice-acetone bath with continued shaking. Sterile lipospheres were prepared by performing all the preparation steps under aseptic conditions and by using only depyrogenated glassware and sterile disposable devices.

EXAMPLE 2: Method of Preparation of Lipospheres Containing the Malaria Antigen R32NS1

The malaria antigens employed in this study R32NS1 (immunization methods) and R32LR (used in ELISA only) were from SmithKline Beecham Pharmaceuticals, Swedeland, Pa. The antigens consist of 30 repeats (R) of the tetrapeptide Asn-Ala-Asn-Pro (NANP) interspersed with two tetrapeptides Asn-Val-Asp-Pro (NVDP). These are repeats from the immunodominant repeat region of the circumsporozoite (CS) protein of *Plasmodium falciparum* linked to an 81 amino acid nonstructural protein of influenza virus (NS1), in the case of R32NS1, and the first two amino acids leucine and arginine (LR) from a tetracycline resistant gene in the case of R32LR.

To a 20 ml vial was added ethyl stearate (200 mg) and L-α-lecithin (100 mg). The vial was heated to 40° C. to melt the ethyl stearate. Warm PBS buffer solution (pH 7.4, 35°–40° C., 10 ml) containing the malaria antigen R32NS1 (0.2 mg/ml) was added and the formulation was mixed well by vigorous hand shaking and by vortexing for about 5 min. The uniform milky-appearing formulation was immediately cooled to a temperature below 20° C. by immersing the vial in a dry ice-acetone bath with continued shaking.

EXAMPLE 3: Method of Preparation of Liposheres Containing Two Immunogens of Markedly Different Chemical Structure: R32NS1 (proterin antigen) and Lipid A (glycophospholipid antigen)

To a 20 ml vial was added ethyl stearate (300 mg) L-α-lecithin (150 mg) and lipid A (2 mg). The vial was heated to 40° C. to melt the ethyl stearate. Warm PBS buffer solution (pH 7.4, 35°–40° C., 10 ml) containing the R32NS1 antigen (0.2 mg/m) was added and the formulation was mixed well by vortexing and hand shaking until an homogeneous milky-appearing formulation was obtained, followed by rapid cooling below 20° C. by immersing the vial in a dry ice-acetone bath with continued shaking.

EXAMPLE 4: Method of Preparation of Liposheres Containing One or More Antigens Incorporated into Liposomes Antigens R32NS and lipid A were encapsulated in multilamellar liposomes composed of dimyristoyl phosphatidyl choline (DMPC), dimyristoyl phosphatidyl glycerol (DMPG) and cholesterol (CHO) at a molar ratio of 9:1:7.5 (final R32NS1 and lipid A concentrations of 1 and 0.2 mg/ml respectively) according to the method described by Alving, et al., "Preparation and use of liposomes in immunological studies." *In Liposome Technology,* Vol. II, G. Gregoriadis, ed., pp. 157–175 (CRC Press, Boca Raton, 1984). To a 20 ml vial was added ethyl stearate (300 mg) and L-α-lecithin (150 mg) and the vial was heated to 40° C. to melt the ethyl stearate. Warm liposome dispersion containing the R32NS1 and lipid A immunogens were added and the formulation was shaken and cooled as described in examples one to three.

EXAMPLE 5: Enzyme-linked Immunosorbent Assay (ELISA) for Evaluation of the IgG Antibody Activity Obtained After Immunization with R32NS1 Malaria Antigen Encapsulated in Liposhere Wells of polystyrene microtiter plates were coated with R32LR antigen (0.1 μg) in PBS. Approximately 18 h later the contents of the wells were aspirated, filled with blocking buffer (0.5% casein, 0.01% thimerosal, 0.005% phenol red and 1% Tween TM 20 in PBS) and held for 1 h at room temperature. Rabbit sera to be tested was diluted in 0.5% blocking buffer containing 0,025% Tween 20, and aliquots of each dilution added to triplicate wells. After a 2 h incubation at room temperature, the contents of the wells were aspirated, washed three times with PBS-Tween TM 20 (0.05%) and 50 μg horseradish peroxidase-conjugated goat anti-human IgG (diluted 1:1000 in 0.5% blocking buffer containing 0.025% Tween TM 20) were added to each well. After 1 h the contents of the wells were aspirated, the wells were washed three times with the PBS-Tween TM 20 washing solution and 100 μl peroxidase substrate was then added to each well. ELISA activity was measured as absorbance at 405 nm 1 h after addition of peroxidase substrate using an automatic ELISA plate reader. ELISA units were calculated by multiplying the absorbance at 405 mm at a given dilution by the reciprocal of the dilution.

EXAMPLE 6: Immunization with Malaria Antigen Encapsulated in Liposheres

Four rabbits were immunized intramuscularly and boosted four weeks later with 0.5 to 1 ml liposheres containing doses of 100 μg R32NS1 malaria antigen and 40 μg lipid A adsorbed with alum (1.0 mg/ml final concentration) as an adjuvant. The animals were bled before primary innnunization and after every two weeks and the sera stored at −20° C. The immune response was determined by measuring the antibody titer, as described in Example 5.

Figure 1A:
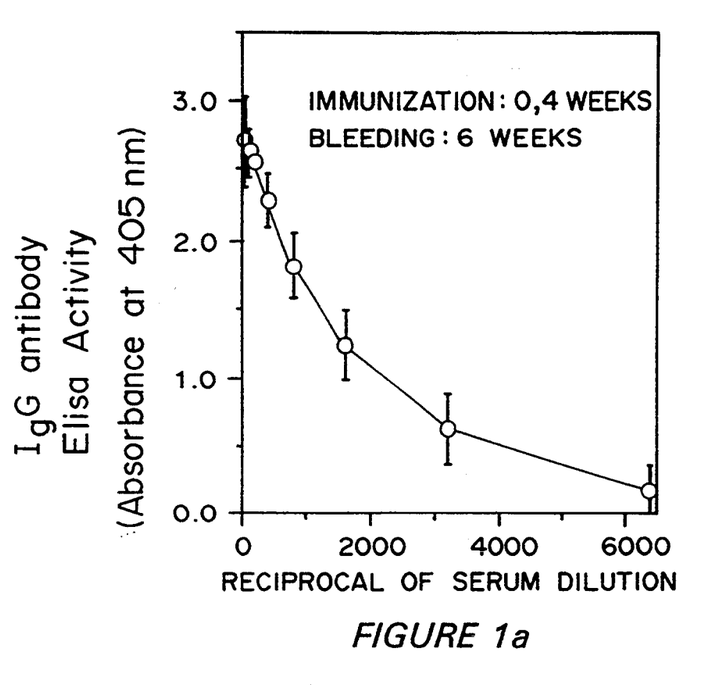
FIG. 1A is a graph of the IgG antibody (ELISA units) against [M(R32NS1 +LA)+Alum] over time following immunization (weeks) for four rabbits immunized intramuscularly at 0 and 4 weeks with 0.5 to 1 ml liposheres containing 100 µg R32NS1 malaria antigen and 40 µg lipid A adsorbed with alum.
Figure 1B:
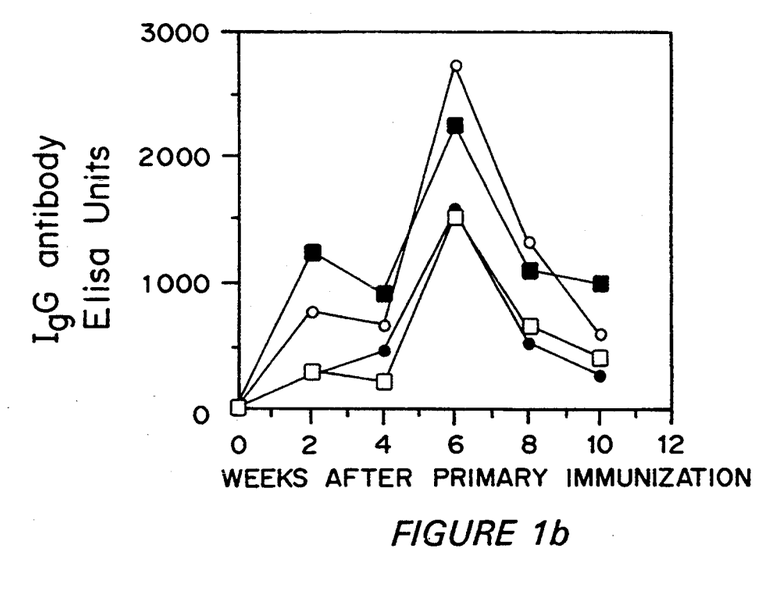
FIG. 1B is a graph of the shows the mean IgG antibody levels (ELISA activity based on absorbance at 405 nm) for the four rabbits six weeks after immunization with liposheres containing the R32NS1 antigen as function of the reciprocal of serum dilution.

The results in FIG. 1A show the increase over time of the anti-malaria antigen IgG antibody in individual rabbits. As demonstrated by this figure, encapsulation of the malaria antigen R32NS1 in liposheres resulted in increased IgG antibody levels in all four rabbits, especially after the boost at 4 weeks. FIG. 1B shows the mean IgG antibody levels for 4 rabbits immunized with liposheres containing the R32NS1 antigen as a function of the reciprocal of serum dilution.

EXAMPLE 7: Immunization with Malaria Antigen Encapsulated in Liposheres: Effect of Lipid A Four groups of 3 rabbits each were immunized intramuscularly at 0 and 4 weeks with four different liposhere formulations (between 0.5 and 1 ml) containing malarial antigens, either M1 and M2, containing lipid A, (10 μg) or M3 and M4 lacking lipid A (10 μg), where the antigen was incorporated in the liposheres from an aqueous buffer solution (M1) or added as a lyophilized powder to the lipid components in the first step of liposhere preparation (M3), at R32NS1 antigen doses of 100 μg adsorbed with alum (1 mg/ml final concentration). The animals were bled and antibody levels determined as described in Examples 5 and 6.

Figure 2A:
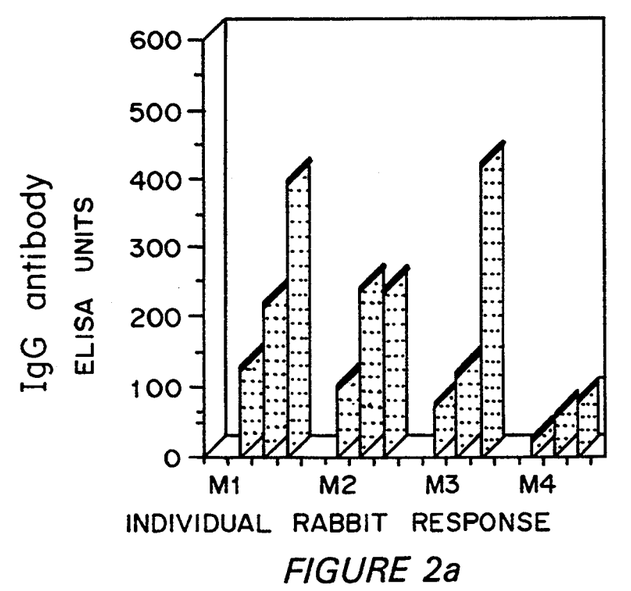
FIG. 2A is a graph of the antibody produced (ELISA units) six weeks after immunization (at zero time and again four weeks later) with lipospere formulations (between 0.5 and 1 ml) containing malarial antigens, M1 and M2, containing lipid A, (10 µg) or M3 and M4 lacking lipid A (10 µg), where the antigen was incorporated in the liposheres from an aqueous buffer solution (M1) or added as a lyophilized powder to the lipid components in the first step of liposphere preparation (M3), at R32NS1 antigen doses of 100 μg adsorbed with alum (1 mg/ml final concentration).

The results obtained at six weeks after primary immunization (2 weeks after boosting at four weeks) are shown in FIG. 2A. Higher levels of IgG antibodies were found for liposheres containing R32NS1 and lipid A as compared to liposheres containing only R32NS1 and lacking lipid A (M2, M4). FIG. 2A also shows that no significant difference (similar geometric means) was observed whether the antigen was incorporated in the liposheres from an aqueous buffer solution (M1) or added as a lyophilized powder to the lipid components in the first step of liposhere preparation (M3).

EXAMPLE 8: Immunization with Malaria Antigert Incorporated in Liposheres Prepared as Described in Example 5

Two groups of three rabbits each were immunized at 0 and 4 weeks by intramuscular injections of between 0.5 to 1 ml of liposheres containing the malaria antigen R32NS1 (100 μg) and lipid A (LM1, 20 μg) or lacking lipid A (LM2). The animals were bled and IgG antibody levels were measured as described in Examples 5 and 9.

Figure 2B:
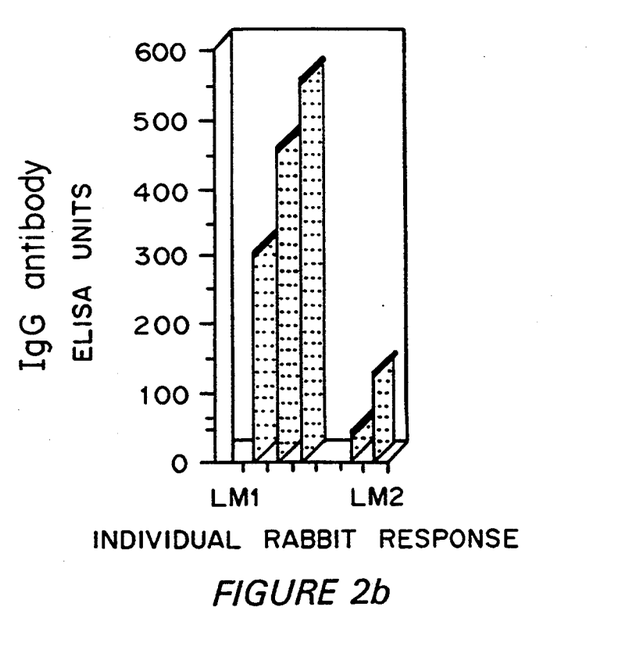
FIG. 2B is a graph of the antibody produced (ELISA units) six weeks after immunization (at zero time and again four weeks later) with between 0.5 to 1 ml of liposheres containing the malaria antigen R32NS1 (100 μg) and lipid A (LM1, 20 μg) or lacking lipid A (LM2).

As shown in FIG. 2B, the IgG antibody levels of individual rabbits were higher for the LM1 lipospheres formulation, containing lipid A as an adjuvant, as compared with the M1-M4 lipospheres, containing alum an adjuvant, and the LM2 lipospheres, not containing adjuvant.

EXAMPLE 9: Enzyme-linked Immunosorbent for Evaluation of the IgG Antibody Activity Obtained After Immunization with Lipospheres Containing Lipid A Lipid A was coated onto the surface of wells in polystyrene microtiter plates by addition of an ethanolic solution (1 μg lipid A/50 μl/well) to the wells, followed by evaporation of the solvent by air under a fume hood. Plates were blocked by addition of PBS containing 10% fetal calf serum (FCS) and incubating the plates for 2 h at room temperature. Well contents were then removed and 50 μl of serum diluted in blocking buffer was added per well (3 replicates) and the plates incubated overnight at 4° C. Plates were then washed 3 times with PBS and 50 μl of goat anti-rabbit IgG (1:500 dilution in blocking buffer, 1 μg/ml) added to the well. Alkaline phosphatase conjugate was added to the wells and incubated 1 h at room temperature. Plates were again washed three times with PBS and 50 μl of the substrate p-nitrophenyl phosphate at 2 mg/ml in diethanolamine buffer was added to the wells and incubated for 1 h at room temperature. Plates were scanned for optical absorbance at 405 nm using an automatic plate reader. Values reported were adjusted by subtracting values in blank wells that lacked both antigen and monoclonal antibody.

The same assay was used to evaluate the IgM antibody levels obtained after immunization with lipospheres containing Lipid A. substituting goat anti-rabbit IgM for the second antibody.

EXAMPLE 10: Immunization with Lipid A and R32NS1 Encapsulated in Lipospheres, and measurement of antibody response to the Lipid A Four rabbits were immunized with lipospheres containing lipid A (40 μg) and R32NS1 (100 μg) at weeks 0 and again after four weeks, and the individual animal immune response to lipid A determined utilizing the procedure for analyzing IgG and IgM antibodies to lipid A described in Examples 5 and 9.

Figure 3A:
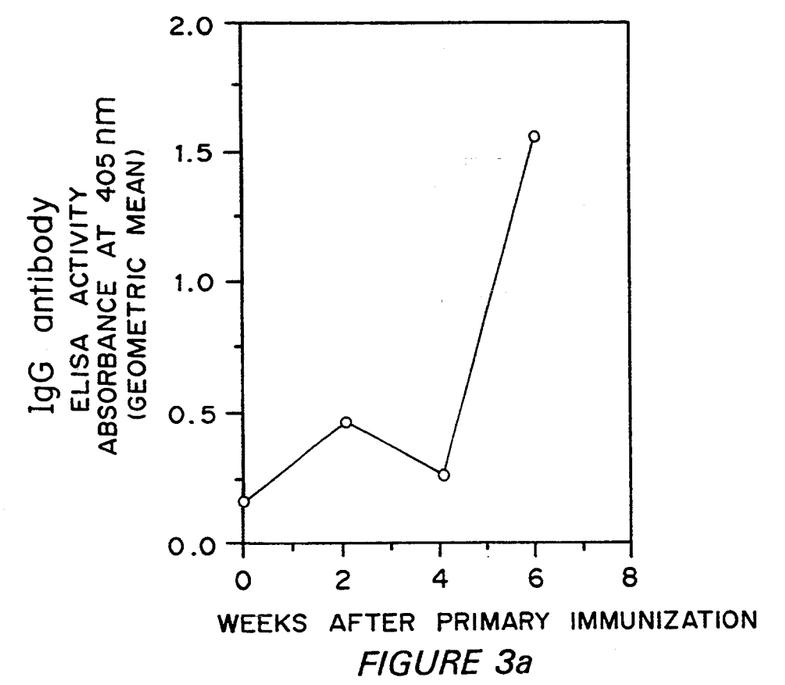
Figure 3B:
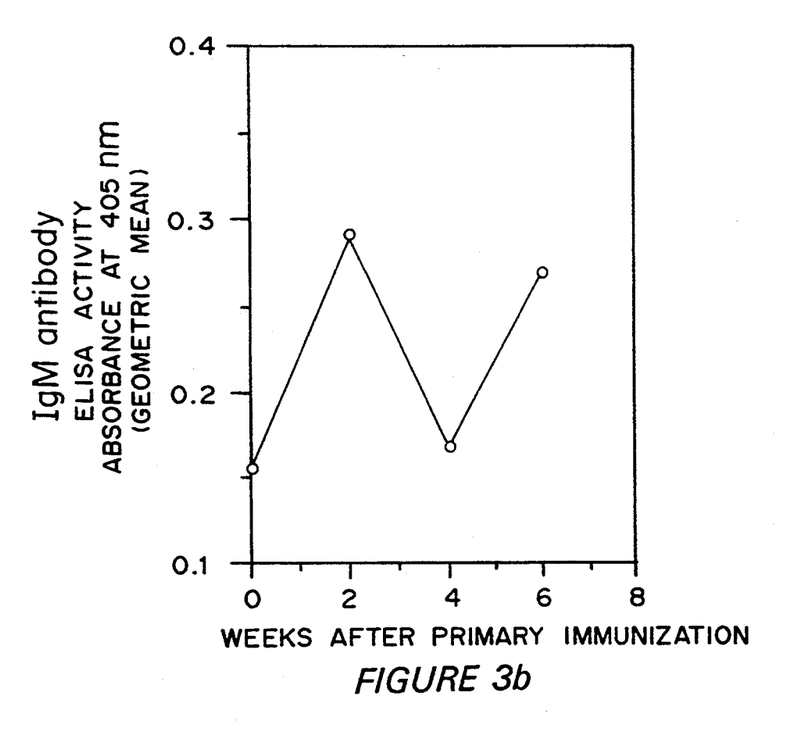

As shown in FIGS. 3A and 3B, encapsulation of lipid A in lipospheres resulted in increased mean IgG and IgM antibody activities, especially after the second immunization four weeks after the primary immunization.

EXAMPLE 11: Toxicity and Pyrogenicity Test of Lipospheres Containing R32NS1 and Lipid A Lipospheres containing R32NS1 (125 μg/dose) and lipid A (60 μg/dose) were injected intramuscularly into 3 rabbits and the rabbits' temperatures measured for two weeks after injection. The animals were also bled daily and whole white and red blood cell counts performed. The results were compared to those observed in rabbits injected with the same dose of free lipid A (60 μg).

Figure 4A:
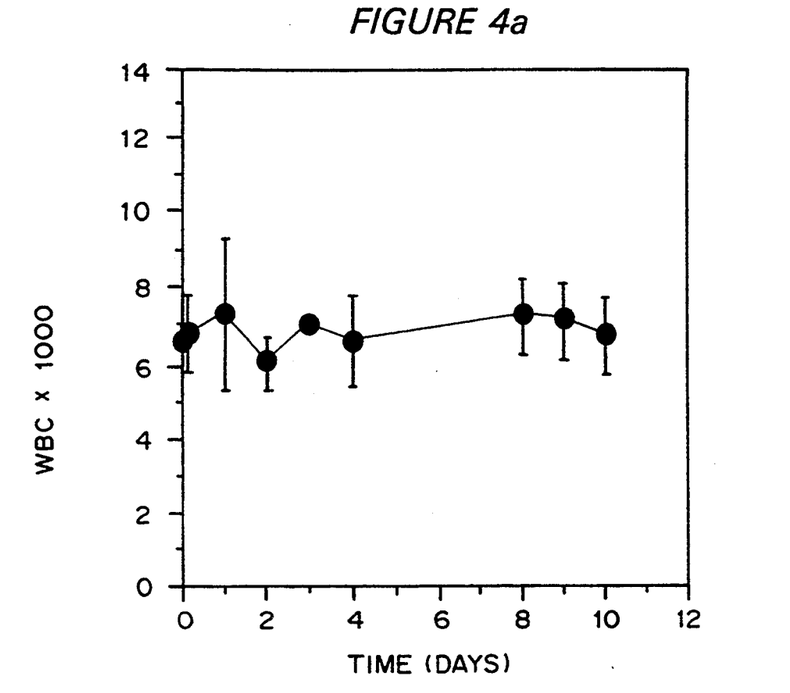
Figure 4B:
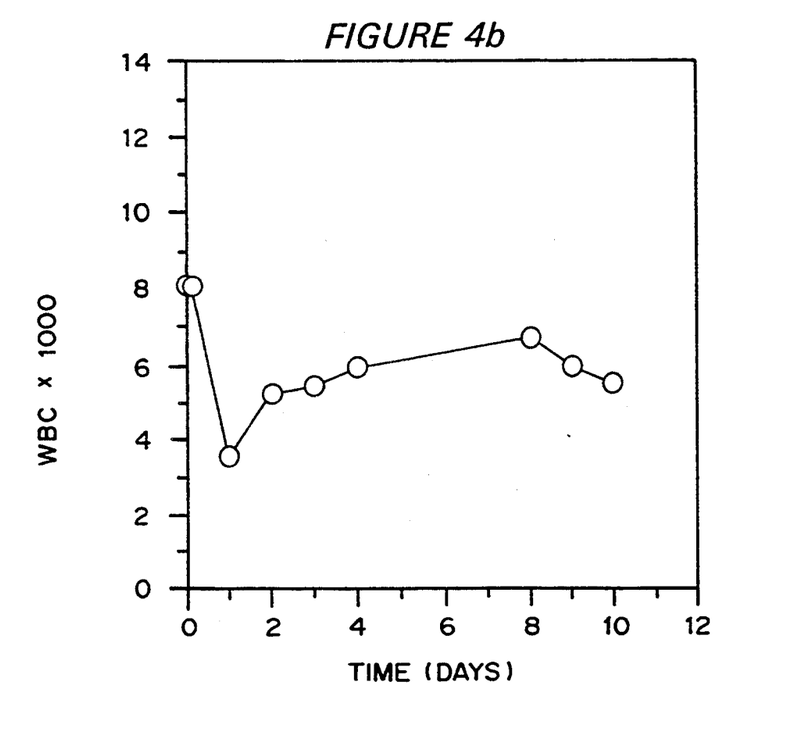

FIG. 4 shows that the number of total white blood cells remained constant up to ten days after the intramuscular injection of lipospheres containing lipid A (FIG. 4A), compared to a pronounced leukopenia observed in rabbits injected with the same amount of free lipid A (FIG. 4B). No pyrogenicity was observed after intramuscular injections of lipid A-encapsulated in lipospheres. The mean rabbit body temperature over the first 10 post injection days was 39.5±0.1, compared to 39.8±0.25 in rabbits injected with the same dose of free lipid A.

EXAMPLE 12: Comparison of the animal immune response obtained using lipospheres and liposomes as carriers of the same antigens Lipospheres containing the malarial antigen R32NS1 and lipid A were prepared as described in example 3. Liposomes containing the malarial antigen R32NS1 (100 μg) and lipid A (40 μg) were prepared as described by Richards, et al., *Infection and Immunity*, 56:682–686 (1988). Detection of IgG antibody activities against malaria antigen after immunization was performed using the ELISA procedures in examples 5 and 9. Animal immunization protocols were as described in example 6.

Rabbits were immunized with either lipospheres or liposomes. The lipospheres and the liposomes were injected intramuscularly into either of two groups of four rabbits; the rabbits were boosted with a second injection four weeks later. Both preparations also contained alum as an additional adjuvant.

Figure 5A:
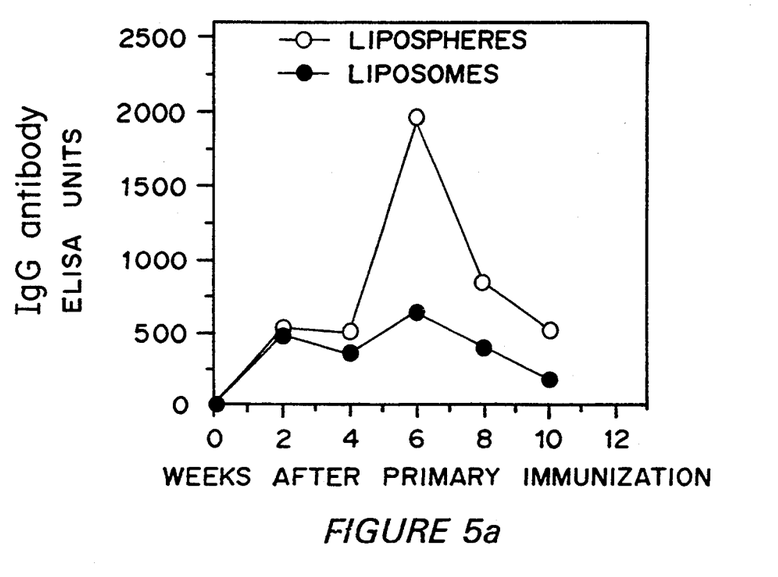

The mean antibody titer for each of the rabbits in the two groups is shown in FIG. 5A. Following the second immunization, the antibody titers in the animals that were injected with the lipospheres were much higher than in those injected with the liposomes. Antigen alone or in the presence of adjuvants produces virtually no titer. The liposomes shown here are the most effective form of delivery for producing a malarial vaccine at this time.

Figure 5B:
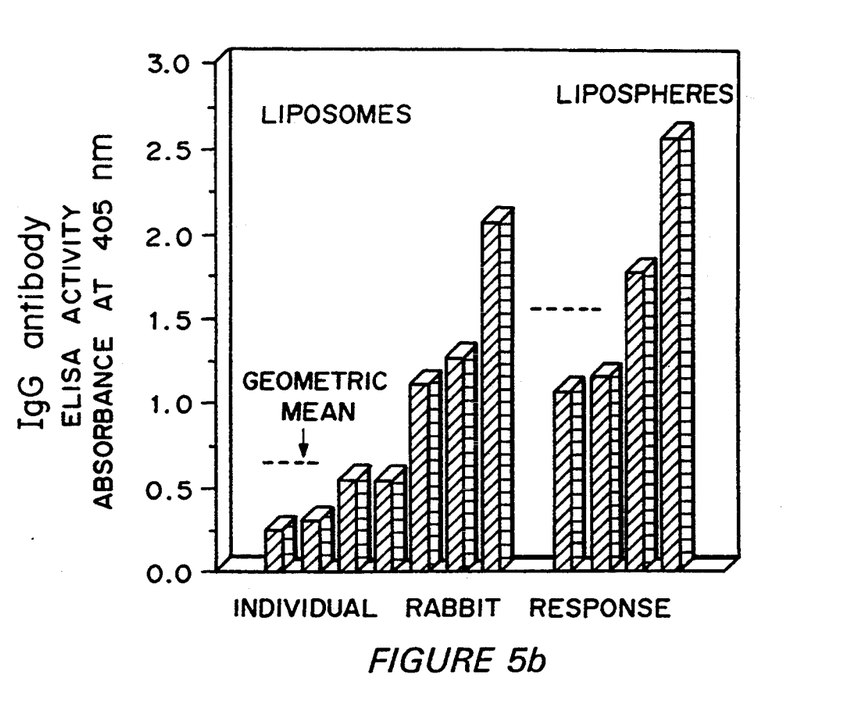

FIG. 5B shows the individual titers of each animal in the two groups. It is important to note that the liposomes do not produce uniformly high titers. The dotted horizontal line in this figure shows the titer obtained in the one human who was subsequently shown to have been protected against intentional infection. Several of the liposome-treated animals have presumably protective levels of IgG, but several did not. In contrast, all of the liposphere-treated animals had presumably protective levels; none of these animals failed to produce high titers.

Modifications and variations of the present invention, a method and compositions for vaccinating animals using an improved delivery system, will be obvious to those skilled in the art from the foregoing detailed description. Such modifications and variations are intended to come within the scope of the appended claims.

We claim:

1. A liposphere comprising:
   a core formed of a hydrophobic material existing as a solid at a temperature of 25° C., and
   a phospholipid coating surrounding the core,
   wherein the hydrophobic ends of the phospholipid are embedded in the solid core and the hydrophilip ends of the phospholipid are exposed on the surface of the liposphere, the combination forming a spherical structure having an average particle diameter between 0.35 and 250 microns, wherein the liposphere contains agents having antigenic activity which elicit a cell mediated immune response or a humoral immune response when administered to a human or animal.

2. The liposphere of claim 1 wherein the solid core comprises the antigen in a vehicle for the antigen, wherein the vehicle in combination with the antigen exists as a solid at 25° C.

3. The liposphere of claim 1 wherein antigen is incorporated into or onto the phospholipid layer.

4. The liposphere of claim 2 wherein the liposphere, or components of the liposphere, has adjuvant activity which increases the immunological response to the antigen.

5. The liposphere of claim 1 wherein the solid core has a melting point between 25° C. and 120° C.

6. The liposphere of claim 2 wherein the vehicle is selected from the group consisting of natural, regenerated and synthetic waxes, fatty acid esters, high molecular weight fatty alcohols, solid hydrogenated plant oils, solid triglyceride, and biodegradable natural and synthetic polymers.

7. The liposphere of claim 4 wherein the adjuvant is derived from or present in a bacterial cell.

8. The liposphere of claim 4 wherein either the antigen or the adjuvant, which increases the immunologicsal response to the antigen, is toxic if administered to a human or animal when not incorporated with the liposphere.

9. The liposphere of claim 1 wherein the antigen is derived from an infectious agent selected from the group consisting of bacterial, virus, parasite, and fungus and the antigen does not elicit antibody production in a human or a animal that is effective in protecting the human or animal against the infectious agent when it is administered to the animal in the absence of the liposphere.

10. The liposphere of claim 1 wherein the antigen is derived from an infectious agent selected from the group consisting of bacteria, viruses, fungi, and parasites.

11. The liposphere of claim 1 wherein the antigen is administered to block an immune response.

12. The liposphere of claim 1 wherein there is more than one antigen incorporated into or onto the liposphere.

13. The liposphere of claim 1 in a pharmaceutically acceptable carrier for enteral administration to a patient.

14. The liposphere of claim 1 in a pharmaceutically acceptable carrier for parenteral administration to a patient.

15. The liposphere of claim 1 in a pharmaceutically acceptable carrier for administration topically to membranes or skin.

16. A method of immunizing an animal comprising administering to the animal liposphere including
a core formed of a hydrophobic material existing as a solid at a temperature of 25° C., and
a phospholipid coating surrounding the core,
wherein the hydrophobic ends of the phospholipid are embedded in the solid core and the hydrophilic ends of the phospholipid are exposed on the surface of the liposphere, the combination forming a spherical structure having an average particle diameter between 0.35 and 250 microns,
wherein the liposphere contains agents having antigenic activity derived from an infectious agent selected from the group consisting of bacteria, viruses, fungi, and parasites,
in a pharmaceutically acceptable carrier.

17. The method of claim 16 wherein the antigen is administered to block an immune response.

18. The method of claim 16 wherein the solid core contains either an antigen or an adjuvant, which increases he immunological response to the antigen, wherein the antigen or adjuvant normally elicits a toxic reaction when administered to the animal without being incorporated within the liposphere.

19. The method of claim 16 wherein the solid core comprises the antigen in a vehicle for the antigen wherein the vehicle in combiation with the antigen, exists as a solid at 25° C.

20. The method of claim 16 wherein the antigen is incoporated into or onto the phospholipid layer.

21. The method of claim 16 wherein the liposphere, or components of the liposphere, have adjuvant activity.

22. The method of claim 16 wherein the lipospheres are formed by adding to a non-aqueous liquid of the hydrophobic core material a phospholipid, and
mixing the liquid core material and phospholipid until a suspension of lipospheres is formed.

23. The method of claim 22 further comprising sonicating and cooling the liquid core material and phospholipid after mixing.

24. The method of claim 22 wherein the hydrophobic core material is liquified by heating.

25. The method of claim 22 wherein the hydrophobic core material is liquified by dissolving the material in solvent.

26. The method of claim 25 wherein the the liquid core material includes an organic solvent, further comprising evaporating the solvent while mixing the core material and phospholipid.

27. The method of claim 23 further comprising adding an aqueous buffer to the evaporated core material-phospholipid mixture and mixing until a suspension of lipospheres is formed.

28. The method of claim 16 comprising administering to an animal more than one antigenic agent in the liposphere.

29. The method of claim 16 wherein the lipospheres are administered parenterally.

30. The method of claim 16 wherein the lipospheres are administered enterally.

31. The method of claim 16 wherein the lipospheres are administered topically to membranes or skin.

* * * * *